United States Patent
Singh et al.

(10) Patent No.: US 9,144,552 B2
(45) Date of Patent: *Sep. 29, 2015

(54) RAPIDLY DISSOLVING FILM FOR DELIVERY OF AN ACTIVE AGENT

(71) Applicants: CORIUM INTERNATIONAL, INC., Menlo Park, CA (US); A.V. TOPCHIEV INSTITUTE OF PETROCHEMICAL SYNTHESIS, RUSSIAN ACADEMY OF SCIENCES, Moscow (RU)

(72) Inventors: Parminder Singh, Union City, CA (US); Sri Mudumba, Union City, CA (US); Danir F. Bayramov, Irvine, CA (US); Valery G. Kulichikhin, Moscow (RU); Mikhail M. Feldstein, Moscow (RU); Gary W. Cleary, Los Altos Hills, CA (US)

(73) Assignees: A.V. Topchiev Institute of Petrochemical Synthesis, Russian Academy of Sciences, Moscow (RU); Corium International, Inc., Menlo Park, CA (US)

( * ) Notice: Subject to any disclaimer, the term of this patent is extended or adjusted under 35 U.S.C. 154(b) by 51 days.

This patent is subject to a terminal disclaimer.

(21) Appl. No.: 14/171,612

(22) Filed: Feb. 3, 2014

(65) Prior Publication Data

US 2014/0147489 A1    May 29, 2014

Related U.S. Application Data

(63) Continuation of application No. 11/047,964, filed on Jan. 31, 2005, now Pat. No. 8,658,201.

(60) Provisional application No. 60/540,852, filed on Jan. 30, 2004.

(51) Int. Cl.
  *A61K 9/70*   (2006.01)
  *A61K 9/46*   (2006.01)
  *A61K 9/00*   (2006.01)

(52) U.S. Cl.
  CPC ............ *A61K 9/7007* (2013.01); *A61K 9/006* (2013.01); *A61K 9/0014* (2013.01); *A61K 9/0056* (2013.01)

(58) Field of Classification Search
  CPC . A61K 9/0002; A61K 9/0053; A61K 9/0056; A61K 9/006
  USPC .......................................... 424/435, 466, 439
  See application file for complete search history.

(56) References Cited

U.S. PATENT DOCUMENTS

| 2,561,071 A | 7/1951 | Prisk |
| 2,579,403 A | 12/1951 | Slomowitz et al. |
| 3,150,977 A | 9/1964 | Hart et al. |
| 3,689,439 A | 9/1972 | Field et al. |
| 3,721,657 A | 3/1973 | Seiderman |
| 3,749,755 A | 7/1973 | Bronstart et al. |
| 3,852,228 A | 12/1974 | Brothers |
| 3,957,605 A | 5/1976 | Assarsson et al. |
| 3,993,551 A | 11/1976 | Assarsson et al. |
| 3,996,934 A | 12/1976 | Zaffaroni |
| 4,091,090 A | 5/1978 | Sipos |
| 4,093,673 A | 6/1978 | Chang et al. |
| 4,160,020 A | 7/1979 | Ayer et al. |
| 4,231,369 A | 11/1980 | Sorensen et al. |
| 4,277,580 A | 7/1981 | Allen et al. |
| 4,325,851 A | 4/1982 | Colon et al. |
| 4,346,709 A | 8/1982 | Schmitt et al. |
| 4,367,732 A | 1/1983 | Poulsen et al. |
| 4,369,229 A | 1/1983 | Shah |
| 4,492,685 A | 1/1985 | Keith et al. |
| 4,529,601 A | 7/1985 | Broberg et al. |
| 4,552,751 A | 11/1985 | Inaba et al. |
| 4,557,934 A | 12/1985 | Cooper |
| 4,562,060 A | 12/1985 | Broberg et al. |
| 4,568,343 A | 2/1986 | Leeper et al. |
| 4,587,289 A | 5/1986 | Comert et al. |
| 4,593,053 A | 6/1986 | Jevne et al. |
| 4,624,665 A | 11/1986 | Nuwayser |
| 4,699,146 A | 10/1987 | Sieverding |
| 4,713,243 A | 12/1987 | Schiraldi et al. |
| 4,743,249 A | 5/1988 | Loveland |
| 4,750,482 A | 6/1988 | Sieverding |
| 4,771,105 A | 9/1988 | Shirai et al. |
| 4,849,224 A | 7/1989 | Chang et al. |

(Continued)

FOREIGN PATENT DOCUMENTS

| CA | 2520986 | 4/2000 |
| CA | 2402021 | 9/2001 |

(Continued)

OTHER PUBLICATIONS

V. Schehlmann (Polyvinlycaprolactam: Physical and cosmetic properties of a new hair fixative resin, Lecture, 1997, SOFW-Journal-Sounderdruck).*
U.S. Appl. No. 11/150,811, filed Jun. 10, 2005, Feldstein et al.
U.S. Appl. No. 12/687,586, filed Jan. 11, 2009, Singh et al.
"Aquasorb® A-500 Cellulose Gum (CMC)", Hercules Incorporated, Aqualon Division, Product Data No. 4234, 2 pgs. (2005).
International Search Report for PCT/US2010/000081 Mailed Sep. 7, 2010.
Aubin et al., "Analysis of the glass transition temperature of miscible polymer blends", Macromolecules, vol. 21, pp. 2945-2949, (1988).

(Continued)

*Primary Examiner* — Michael G Hartley
*Assistant Examiner* — Micah-Paul Young
(74) *Attorney, Agent, or Firm* — Judy M. Mohr; McDermott Will & Emery LLP

(57) ABSTRACT

A rapidly dissolving film is provided for delivery of an active agent to a moist body surface, e.g., mucosal tissue. The film comprises a film-forming binder, a rapidly dissolving polymeric material, and an active agent.

47 Claims, No Drawings

(56) References Cited

U.S. PATENT DOCUMENTS

| | | |
|---|---|---|
| 4,863,738 A | 9/1989 | Taskovich |
| 4,863,970 A | 9/1989 | Patel et al. |
| 4,867,748 A | 9/1989 | Samuelsen |
| 4,871,536 A | 10/1989 | Arraudeau et al. |
| 4,873,299 A | 10/1989 | Nawoakosky et al. |
| 4,877,628 A | 10/1989 | Stypula |
| 4,904,247 A | 2/1990 | Therriault et al. |
| 4,906,169 A | 3/1990 | Chien et al. |
| 4,927,408 A | 5/1990 | Haak et al. |
| 4,945,084 A | 7/1990 | Packman |
| 4,953,053 A | 8/1990 | Pratt |
| 4,973,468 A | 11/1990 | Chiang et al. |
| 4,983,395 A | 1/1991 | Chang et al. |
| 5,023,084 A | 6/1991 | Chien et al. |
| 5,053,227 A | 10/1991 | Chiang et al. |
| 5,057,500 A | 10/1991 | Thornfelt |
| 5,073,381 A | 12/1991 | Ivan et al. |
| 5,102,662 A | 4/1992 | Gallagher |
| 5,125,894 A | 6/1992 | Phipps et al. |
| 5,133,970 A | 7/1992 | Petereit et al. |
| 5,141,750 A | 8/1992 | Lee et al. |
| 5,173,302 A | 12/1992 | Holmblad et al. |
| 5,183,901 A | 2/1993 | Login et al. |
| 5,196,405 A | 3/1993 | Packman |
| 5,200,190 A | 4/1993 | Azuma et al. |
| 5,206,385 A | 4/1993 | Login et al. |
| 5,224,928 A | 7/1993 | Sibalis et al. |
| 5,232,702 A | 8/1993 | Pfister et al. |
| 5,234,690 A | 8/1993 | Chiang et al. |
| 5,234,957 A | 8/1993 | Mantelle |
| 5,240,995 A | 8/1993 | Gyory et al. |
| 5,254,346 A | 10/1993 | Tucker et al. |
| 5,270,358 A | 12/1993 | Asmus |
| 5,276,079 A | 1/1994 | Duan et al. |
| 5,296,512 A | 3/1994 | Beier et al. |
| 5,300,291 A | 4/1994 | Sablotsky et al. |
| 5,310,563 A | 5/1994 | Curtis et al. |
| 5,322,689 A | 6/1994 | Hughes et al. |
| 5,326,685 A | 7/1994 | Gaglio et al. |
| 5,332,576 A | 7/1994 | Mantelle |
| 5,338,490 A | 8/1994 | Dietz et al. |
| 5,342,623 A | 8/1994 | Enscore et al. |
| 5,344,394 A | 9/1994 | Gyory et al. |
| 5,354,823 A | 10/1994 | Tseng et al. |
| 5,362,420 A | 11/1994 | Itoh et al. |
| 5,376,377 A | 12/1994 | Gale et al. |
| 5,422,119 A | 6/1995 | Casper |
| 5,438,076 A | 8/1995 | Friedman et al. |
| 5,446,070 A | 8/1995 | Mantelle |
| 5,456,745 A | 10/1995 | Roreger et al. |
| 5,462,743 A | 10/1995 | Turner et al. |
| 5,462,745 A | 10/1995 | Enscore et al. |
| 5,492,943 A | 2/1996 | Stempel |
| 5,508,024 A | 4/1996 | Tranner |
| 5,508,367 A | 4/1996 | Zajaczkowski |
| 5,527,271 A | 6/1996 | Shah et al. |
| 5,543,148 A | 8/1996 | Lapidus |
| 5,563,153 A | 10/1996 | Mueller et al. |
| 5,575,654 A | 11/1996 | Fontenot |
| 5,593,686 A | 1/1997 | Kissel et al. |
| 5,594,068 A | 1/1997 | Buchanan et al. |
| 5,599,373 A | 2/1997 | Zanuccoli |
| 5,614,178 A | 3/1997 | Bloom et al. |
| 5,631,267 A | 5/1997 | Gleich et al. |
| 5,633,010 A | 5/1997 | Chen |
| 5,641,504 A | 6/1997 | Lee et al. |
| 5,641,507 A | 6/1997 | DeVillez |
| 5,643,187 A | 7/1997 | Naestoft et al. |
| 5,645,062 A | 7/1997 | Anderson et al. |
| 5,645,855 A | 7/1997 | Lorenz |
| 5,656,286 A | 8/1997 | Miranda et al. |
| 5,660,178 A | 8/1997 | Kantner et al. |
| 5,662,925 A | 9/1997 | Ebert et al. |
| 5,663,010 A | 9/1997 | Stocchiero |
| 5,674,561 A | 10/1997 | Dietz et al. |
| 5,700,478 A | 12/1997 | Biegajski et al. |
| 5,702,721 A | 12/1997 | Horstmann et al. |
| 5,718,187 A | 2/1998 | Pollock et al. |
| 5,718,886 A | 2/1998 | Pellico |
| 5,719,197 A | 2/1998 | Kanios et al. |
| 5,723,145 A | 3/1998 | Shikinami et al. |
| 5,725,876 A | 3/1998 | Mantelle et al. |
| 5,726,250 A | 3/1998 | Zajaczkowski |
| 5,730,999 A | 3/1998 | Lehmann et al. |
| 5,744,155 A | 4/1998 | Friedman et al. |
| 5,762,956 A | 6/1998 | Chien |
| 5,770,220 A | 6/1998 | Meconi et al. |
| 5,773,490 A | 6/1998 | Shikinami et al. |
| 5,780,050 A | 7/1998 | Jain et al. |
| 5,785,527 A | 7/1998 | Jensen et al. |
| 5,785,976 A | 7/1998 | Westesen et al. |
| 5,788,983 A | 8/1998 | Chien et al. |
| 5,800,832 A | 9/1998 | Tapolsky et al. |
| 5,804,611 A | 9/1998 | Takoh et al. |
| 5,827,213 A | 10/1998 | Jensen |
| 5,827,525 A | 10/1998 | Liao et al. |
| 5,830,932 A | 11/1998 | Kay |
| 5,837,713 A | 11/1998 | Gleich et al. |
| 5,843,472 A | 12/1998 | Ma et al. |
| 5,846,558 A | 12/1998 | Nielsen et al. |
| 5,851,549 A | 12/1998 | Svec |
| 5,853,755 A | 12/1998 | Foldvari |
| 5,857,992 A | 1/1999 | Haak et al. |
| 5,858,332 A | 1/1999 | Jensen et al. |
| 5,858,410 A | 1/1999 | Muller et al. |
| 5,863,662 A | 1/1999 | Hornby et al. |
| 5,876,746 A | 3/1999 | Jona et al. |
| 5,879,691 A | 3/1999 | Sagel et al. |
| 5,879,701 A | 3/1999 | Audett et al. |
| 5,891,453 A | 4/1999 | Sagel et al. |
| 5,894,017 A | 4/1999 | Sagel et al. |
| 5,900,249 A | 5/1999 | Smith |
| 5,902,598 A | 5/1999 | Chen et al. |
| 5,911,980 A | 6/1999 | Samour et al. |
| 5,912,271 A | 6/1999 | Brodin et al. |
| 5,916,587 A | 6/1999 | Min et al. |
| 5,942,543 A | 8/1999 | Ernst |
| 5,945,032 A | 8/1999 | Breitenbach et al. |
| 5,945,457 A | 8/1999 | Plate et al. |
| 5,948,416 A | 9/1999 | Wagner et al. |
| 5,948,430 A | 9/1999 | Zerbe et al. |
| 5,948,433 A | 9/1999 | Burton et al. |
| 5,958,379 A | 9/1999 | Regenold et al. |
| 5,958,446 A | 9/1999 | Miranda et al. |
| 5,958,984 A | 9/1999 | Devillez |
| 5,962,011 A | 10/1999 | DeVillez |
| 5,972,377 A | 10/1999 | Jona et al. |
| 5,976,565 A | 11/1999 | Fotinos |
| 5,985,311 A | 11/1999 | Cordes et al. |
| 5,985,860 A | 11/1999 | Toppo |
| 5,985,990 A | 11/1999 | Kantner et al. |
| 5,989,569 A | 11/1999 | Dirksing et al. |
| 5,990,179 A | 11/1999 | Gyori et al. |
| 5,993,836 A | 11/1999 | Castillo |
| 5,993,849 A | 11/1999 | Assmus et al. |
| 5,997,886 A | 12/1999 | Peffly et al. |
| 6,004,566 A | 12/1999 | Friedman et al. |
| 6,004,578 A | 12/1999 | Lee et al. |
| 6,007,837 A | 12/1999 | Enscore et al. |
| 6,024,976 A | 2/2000 | Miranda et al. |
| 6,045,811 A | 4/2000 | Dirksing et al. |
| 6,051,609 A | 4/2000 | Yu et al. |
| 6,063,399 A | 5/2000 | Assmus et al. |
| 6,068,650 A | 5/2000 | Hofmann et al. |
| 6,072,100 A | 6/2000 | Mooney et al. |
| 6,075,626 A | 6/2000 | Mizutani et al. |
| 6,083,421 A | 7/2000 | Huang et al. |
| 6,093,328 A | 7/2000 | Santina |
| 6,096,328 A | 8/2000 | Sagel et al. |
| 6,135,126 A | 10/2000 | Joshi |
| 6,142,939 A | 11/2000 | Eppstein et al. |
| 6,146,654 A | 11/2000 | Kubo |
| 6,153,215 A | 11/2000 | Samuelsen et al. |
| 6,162,456 A | 12/2000 | Dunbar et al. |

(56) References Cited

U.S. PATENT DOCUMENTS

| | | | |
|---|---|---|---|
| 6,165,499 A | 12/2000 | Kleinsorgen et al. |
| 6,177,096 B1 | 1/2001 | Zerbe et al. |
| 6,193,993 B1 | 2/2001 | Murahashi et al. |
| 6,197,331 B1 | 3/2001 | Lerner et al. |
| 6,201,164 B1 | 3/2001 | Wulff et al. |
| 6,212,671 B1 | 4/2001 | Kanehira et al. |
| 6,221,341 B1 | 4/2001 | Montgomery |
| 6,221,383 B1 | 4/2001 | Miranda et al. |
| 6,231,885 B1 | 5/2001 | Carrara |
| 6,248,363 B1 | 6/2001 | Patel et al. |
| 6,264,981 B1 | 7/2001 | Zhang et al. |
| 6,270,792 B1 | 8/2001 | Guillemet et al. |
| 6,275,728 B1 | 8/2001 | Venkatraman et al. |
| 6,306,370 B1 | 10/2001 | Jensen et al. |
| 6,312,666 B1 | 11/2001 | Oxman et al. |
| 6,312,670 B1 | 11/2001 | Montgomery |
| 6,316,022 B1 | 11/2001 | Mantelle et al. |
| 6,322,774 B1 | 11/2001 | Jensen et al. |
| 6,329,472 B1 | 12/2001 | Kim et al. |
| 6,368,576 B1 | 4/2002 | Jensen et al. |
| 6,419,905 B1 | 7/2002 | Alvarez Hernandez |
| 6,419,906 B1 | 7/2002 | Xu et al. |
| 6,451,240 B1 | 9/2002 | Sherman et al. |
| 6,451,777 B1 | 9/2002 | Bradbury et al. |
| 6,461,636 B1 | 10/2002 | Arth et al. |
| 6,488,913 B2 | 12/2002 | Orlowski et al. |
| 6,517,350 B2 | 2/2003 | Diasti et al. |
| 6,552,147 B2 | 4/2003 | Parker et al. |
| 6,558,654 B2 | 5/2003 | McLaughlin |
| 6,562,363 B1 | 5/2003 | Mantelle et al. |
| 6,576,712 B2 | 6/2003 | Feldstein et al. |
| 6,585,997 B2 | 7/2003 | Moro et al. |
| 6,591,124 B2 | 7/2003 | Sherman et al. |
| 6,596,298 B2 | 7/2003 | Leung et al. |
| 6,602,912 B2 | 8/2003 | Hsu et al. |
| 6,611,706 B2 | 8/2003 | Avrahami et al. |
| 6,638,528 B1 | 10/2003 | Kanios |
| 6,656,493 B2 | 12/2003 | Dzija |
| 6,667,410 B2 | 12/2003 | Magnus et al. |
| 6,673,363 B2 | 1/2004 | Luo et al. |
| 6,682,721 B2 | 1/2004 | Kim et al. |
| 6,689,344 B2 | 2/2004 | Chang et al. |
| 6,696,459 B1 | 2/2004 | Jones et al. |
| 6,708,060 B1 | 3/2004 | Avrahami et al. |
| 6,709,671 B2 | 3/2004 | Zerbe et al. |
| 6,711,435 B2 | 3/2004 | Avrahami |
| 6,714,497 B2 | 3/2004 | Yeo et al. |
| 6,750,291 B2 | 6/2004 | Kim et al. |
| 6,759,030 B2 | 7/2004 | Kosti |
| 6,762,202 B2 | 7/2004 | Marek et al. |
| 6,780,401 B2 | 8/2004 | Chang et al. |
| 6,783,769 B1 | 8/2004 | Arth et al. |
| 6,803,420 B2 | 10/2004 | Cleary et al. |
| 6,805,874 B1 | 10/2004 | Lutz et al. |
| 6,806,308 B2 | 10/2004 | Zajac |
| 6,884,833 B2 | 4/2005 | Cheang et al. |
| 6,946,142 B2 | 9/2005 | Chang et al. |
| 6,962,691 B1 | 11/2005 | Lulla et al. |
| 7,078,359 B2 | 7/2006 | Stepanian et al. |
| 7,112,713 B2 | 9/2006 | Sceusa |
| 7,122,199 B2 | 10/2006 | Sagel et al. |
| 7,138,458 B2 | 11/2006 | Cleary et al. |
| 7,217,853 B2 | 5/2007 | Kulichikhin et al. |
| 7,323,161 B2 | 1/2008 | Choi et al. |
| 7,384,650 B2 | 6/2008 | Chien |
| 7,456,331 B2 | 11/2008 | Kulichikhin et al. |
| 7,744,918 B2 | 6/2010 | Yamaguchi et al. |
| 8,206,738 B2 | 6/2012 | Singh et al. |
| 8,273,405 B2 | 9/2012 | Feldstein et al. |
| 8,481,059 B2 | 7/2013 | Cleary et al. |
| 8,481,071 B2 | 7/2013 | Singh et al. |
| 8,541,021 B2 | 9/2013 | Singh et al. |
| 8,617,647 B2 | 12/2013 | Feldstein et al. |
| 2001/0006677 A1 | 7/2001 | Mcginity et al. |
| 2001/0021374 A1 | 9/2001 | Montgomery |
| 2001/0022964 A1 | 9/2001 | Leung et al. |
| 2001/0046471 A1 | 11/2001 | Marek et al. |
| 2001/0046511 A1 | 11/2001 | Zerbe et al. |
| 2002/0004065 A1 | 1/2002 | Kanios |
| 2002/0004190 A1 | 1/2002 | Diasti et al. |
| 2002/0006387 A1 | 1/2002 | Sagel et al. |
| 2002/0009420 A1 | 1/2002 | McLaughlin |
| 2002/0032240 A1 | 3/2002 | Hsu et al. |
| 2002/0048602 A1 | 4/2002 | Flore et al. |
| 2002/0058936 A1 | 5/2002 | Avrahami et al. |
| 2002/0076487 A1 | 6/2002 | Zajac |
| 2002/0094426 A1 | 7/2002 | Stepanian et al. |
| 2002/0106335 A1 | 8/2002 | Orlowski et al. |
| 2002/0120170 A1 | 8/2002 | Magnus et al. |
| 2002/0131990 A1 | 9/2002 | Barkalow et al. |
| 2002/0169411 A1 | 11/2002 | Sherman et al. |
| 2002/0197284 A1 | 12/2002 | Luo et al. |
| 2003/0035841 A1 | 2/2003 | Dzija et al. |
| 2003/0044446 A1 | 3/2003 | Moro et al. |
| 2003/0055190 A1 | 3/2003 | Parker et al. |
| 2003/0059381 A1 | 3/2003 | Goodhart et al. |
| 2003/0067855 A1 | 4/2003 | Yeo et al. |
| 2003/0068376 A1* | 4/2003 | Chen et al. ............... 424/484 |
| 2003/0082114 A1 | 5/2003 | Kim et al. |
| 2003/0097127 A1 | 5/2003 | Avrahami |
| 2003/0100654 A1 | 5/2003 | Cheang et al. |
| 2003/0101507 A1 | 6/2003 | Cleary et al. |
| 2003/0103427 A1 | 6/2003 | Yeo et al. |
| 2003/0104041 A1 | 6/2003 | Hsu et al. |
| 2003/0130427 A1 | 7/2003 | Cleary et al. |
| 2003/0133884 A1 | 7/2003 | Chang et al. |
| 2003/0152528 A1 | 8/2003 | Singh et al. |
| 2003/0152615 A1 | 8/2003 | Houze et al. |
| 2003/0170308 A1 | 9/2003 | Cleary et al. |
| 2003/0180229 A1 | 9/2003 | Kosti |
| 2003/0194382 A1 | 10/2003 | Chang et al. |
| 2003/0199644 A1 | 10/2003 | Kim et al. |
| 2003/0225356 A1 | 12/2003 | Kulichikhin et al. |
| 2003/0235549 A1 | 12/2003 | Singh et al. |
| 2004/0005277 A1 | 1/2004 | Willison et al. |
| 2004/0053901 A1 | 3/2004 | Chien |
| 2004/0105834 A1 | 6/2004 | Singh et al. |
| 2004/0136927 A1 | 7/2004 | Kim et al. |
| 2004/0166147 A1 | 8/2004 | Lundy et al. |
| 2004/0181183 A1 | 9/2004 | Sceusa |
| 2004/0186132 A1 | 9/2004 | Jones et al. |
| 2004/0213744 A1 | 10/2004 | Lulla et al. |
| 2004/0219111 A1 | 11/2004 | Kim et al. |
| 2004/0219113 A1 | 11/2004 | Choi et al. |
| 2004/0230227 A1 | 11/2004 | Avrahami et al. |
| 2004/0258723 A1 | 12/2004 | Singh et al. |
| 2005/0031554 A1 | 2/2005 | Kim et al. |
| 2005/0113510 A1 | 5/2005 | Feldstein et al. |
| 2005/0208110 A1 | 9/2005 | Singh et al. |
| 2005/0215727 A1 | 9/2005 | Feldstein et al. |
| 2005/0228113 A1 | 10/2005 | Baumer et al. |
| 2005/0251088 A1 | 11/2005 | Kwon |
| 2005/0256223 A1 | 11/2005 | Kolb et al. |
| 2006/0034905 A1 | 2/2006 | Singh et al. |
| 2006/0089674 A1 | 4/2006 | Walters et al. |
| 2006/0110434 A1 | 5/2006 | Yamaguchi et al. |
| 2006/0168905 A1 | 8/2006 | Blanc et al. |
| 2006/0171906 A1 | 8/2006 | Singh et al. |
| 2006/0182788 A1 | 8/2006 | Singh et al. |
| 2006/0193793 A1 | 8/2006 | Kim et al. |
| 2006/0193794 A1 | 8/2006 | Kim et al. |
| 2006/0257463 A1 | 11/2006 | Elsohly et al. |
| 2008/0161492 A1 | 7/2008 | Cleary et al. |
| 2009/0155343 A1 | 6/2009 | Kawahara et al. |
| 2009/0258060 A1 | 10/2009 | Cleary et al. |
| 2012/0027695 A1 | 2/2012 | Feldstein et al. |
| 2012/0237579 A1 | 9/2012 | Singh et al. |
| 2012/0321569 A1 | 12/2012 | Feldstein et al. |

FOREIGN PATENT DOCUMENTS

| | | |
|---|---|---|
| CA | 2451431 | 1/2003 |
| CA | 2506073 | 6/2004 |
| CA | 2515128 A1 | 8/2004 |

(56) References Cited

FOREIGN PATENT DOCUMENTS

| | | |
|---|---|---|
| CA | 2579492 | 3/2006 |
| DE | 8509793 | 5/1985 |
| DE | 4219368 | 6/1992 |
| EP | 0184470 | 6/1986 |
| EP | 0303445 | 2/1989 |
| EP | 0364211 | 4/1990 |
| EP | 0371421 | 6/1990 |
| EP | 0511782 | 11/1992 |
| EP | 0516026 | 12/1992 |
| EP | 0545594 | 6/1993 |
| EP | 0581581 | 2/1994 |
| EP | 0672094 | 9/1995 |
| EP | 0737477 | 10/1996 |
| EP | 0838225 | 4/1998 |
| EP | 0848960 | 6/1998 |
| EP | 1066823 | 1/2001 |
| EP | 2005952 A1 | 12/2008 |
| GB | 1108837 | 4/1968 |
| JP | 58-162681 | 9/1983 |
| JP | 59-196817 | 11/1984 |
| JP | 01-151524 A | 6/1989 |
| JP | 03-066612 | 3/1991 |
| JP | 03-247334 | 5/1991 |
| JP | 03-275619 | 6/1991 |
| JP | 04-266818 | 9/1992 |
| JP | 06-100467 | 4/1994 |
| JP | 10-017448 | 1/1998 |
| JP | 2001-213768 A | 7/2001 |
| JP | 2002-029949 | 1/2002 |
| JP | 2002-145746 A | 5/2002 |
| KR | 20020045224 | 6/2002 |
| KR | 20030000299 | 1/2003 |
| KR | 20030000528 | 1/2003 |
| KR | 20030003969 | 1/2003 |
| KR | 20030003973 | 1/2003 |
| SU | 1459215 | 11/1995 |
| WO | WO 89/03859 | 5/1989 |
| WO | WO 8903859 A1 * | 5/1989 |
| WO | WO 90/07940 A1 | 7/1990 |
| WO | WO 93/02717 | 2/1993 |
| WO | WO 94/05340 | 3/1994 |
| WO | WO 96/19205 | 6/1996 |
| WO | WO 97/11676 | 4/1997 |
| WO | WO 98/20862 A1 | 5/1998 |
| WO | WO 98/26763 A1 | 6/1998 |
| WO | WO 98/37870 | 9/1998 |
| WO | WO 98/55044 | 12/1998 |
| WO | WO 99/11728 A1 | 3/1999 |
| WO | WO 99/17738 | 4/1999 |
| WO | WO 99/44678 | 9/1999 |
| WO | WO 99/47128 | 9/1999 |
| WO | WO 99/54422 | 10/1999 |
| WO | WO 99/55312 A2 | 11/1999 |
| WO | WO 00/16725 | 3/2000 |
| WO | WO 00/18365 A2 | 4/2000 |
| WO | WO 00/61120 A1 | 10/2000 |
| WO | WO 00/69421 | 11/2000 |
| WO | WO 01/01958 A1 | 1/2001 |
| WO | WO 01/07018 A1 | 2/2001 |
| WO | WO 01/26637 | 4/2001 |
| WO | WO 01/68045 | 9/2001 |
| WO | WO 01/87276 | 11/2001 |
| WO | WO 02/00182 A3 | 1/2002 |
| WO | WO 02/04570 | 1/2002 |
| WO | WO 02/43657 A2 | 6/2002 |
| WO | WO 02/087642 | 11/2002 |
| WO | WO 02/087645 | 11/2002 |
| WO | WO 02/089849 | 11/2002 |
| WO | WO 02089849 A1 * | 11/2002 |
| WO | WO 03/000216 | 1/2003 |
| WO | WO 03/011259 A1 | 2/2003 |
| WO | WO 03/099344 | 12/2003 |
| WO | WO 03/101357 A1 | 12/2003 |
| WO | WO 2004/000389 A2 | 12/2003 |
| WO | WO 2004/024224 A1 | 3/2004 |
| WO | WO 2004/045569 | 6/2004 |
| WO | WO 2004/054638 | 7/2004 |
| WO | WO 2004/071323 | 8/2004 |
| WO | WO 03/089046 | 10/2004 |
| WO | WO 2004/093786 | 11/2004 |
| WO | WO 2004/103201 | 12/2004 |
| WO | WO 2005/027768 | 3/2005 |
| WO | WO 2005/074894 A1 | 8/2005 |
| WO | WO 2006/017807 | 2/2006 |
| WO | WO 2006/029407 | 3/2006 |
| WO | WO 2006/069236 | 6/2006 |
| WO | WO 2006/074173 | 7/2006 |
| WO | WO 2006/081497 | 8/2006 |
| WO | WO 2006/124639 | 11/2006 |
| WO | WO 2007/119656 | 10/2007 |
| WO | WO 2010/083035 | 7/2010 |

OTHER PUBLICATIONS

Bairamov et al., "Kinetic parameters of poly(N-vinyl pyrrolidone) spontaneous mixing with short-chain chain poly(ethylene glycol)", Polym. Mater. Sci. Eng., vol. 82, pp. 7-8, (2000).

Barbucci et al. "Swelling behavior of carboxymethylcellulose hydrogels in relation to cross-linking, pH, and charge density", Macromolecules, vol. 33, No. 20, pp. 7475-7480 (2000).

Borodulina et al. "Viscoelasticity of Pressure-sensitive adhesive and bioadhesive hydrogels under compressive load", Proceed. 24th Annual Meeting Adhesion Soc., pp. 147-149, (2001).

Chalykh et al., "Effects of composition and hydration on adhesive properties of poly(N-vinyl pyrrolidone)-poly(ethylene glycol) hydrogels", Polym. Mater. Sci. Eng., vol. 81, pp. 456-457, (1999).

Chalykh et al., "Fracture mechanics of poly(N-vinyl pyrrolidone)-poly(ethylene glycol) hydrogel adhesive joints," Polym. Mater. Sci. Eng., vol. 81, pp. 427-428, (1999).

Chalykh et al., "Pressure-sensitive adhesion in the blends of poly(N-vinyl pyrrolidone) and poly(ethylene glycol) of disparate chain lengths," J. Adhesion, vol. 78, pp. 667-694, (2002).

Cleary et. al., A new polymer blend adhesive with combined properties to adhere to either skin or mucosa for drug delivery, podium abstract, 30th Annual Meeting and Exposition of the Controlled Release Society, Glasgow, Scotland, Jul. 19-23, 2003, Abstract #123.

Database WPI Section Ch, Week 198451, Derwent Publications Ltd., London, GB; Class A96, AN 1984-315114 & JP 59196817 A (Sekisuki Chem Ind Co Ltd) Nov. 8, 1984 abstract.

Database WPI Section Ch, Week 199150, Derwent Publications Ltd., London, GB; Class A18, AN 1991-366353 & JP 03247334 A (Sumitomo Rubber Ind Ltd) Nov. 5, 1991 abstract.

Database WPI Section Ch, Week 199118, Derwent Publications Ltd., London, GB; Class A96, AN 1991-128478 & JP 03066612 A (Sato Pharm Co Ltd) Mar. 22, 1991 abstract.

Database WPI Section Ch, Week 199627, Derwent Publications Ltd., London, GB; Class A14, AN 1996-266746 & SU 1459215 A ( A Med Cardiology Res Centre) Nov. 20, 1995 abstract.

Emla Cream, (lidocaine 2.5% and prilocaine 2.5%), EMLA Anesthetic Disc, (lidocaine 2.5% and prilocaine 2.5% cream), "Topical anesthetic for dermal analgesia", AstraZeneca Product Monograph, 46 pgs, Revised May 25, 2010.

Feldstein et al., "A structure-property relationship and quantitative approach to the development of universal transdermal drug delivery system," NBC Risks, vol. 25, pp. 441-458, (1999).

Feldstein et al., "Coherence of thermal transitions in poly(N-vinyl pyrrolidone)-poly(ethylene glycol) compatible blends: 1. Interrelations among the temperatures of melting, maximum cold crystalization rate and glass transition", Polymer, vol. 41, pp. 5327-5338, (2000).

Feldstein et al., "Coherence of thermal transitions in poly(N-vinyl pyrrolidone)-poly(ethylene glycol) compatible blends: 2. The temperature of maximum cold crystalization rate versus glass transition", Polymer, vol. 41, pp. 5339-5348, (2000).

Feldstein et al., "Coherence of thermal transitions in poly(N-vinyl pyrrolidone)-poly(ethylene glycol) compatible blends: 3. Impact of sorbed water upon phase behavior", Polymer, vol. 41, pp. 5349-5359, (2000).

(56) References Cited

OTHER PUBLICATIONS

Feldstein et al., "Correlations between activation energy for debonding and that for self-diffusion in pressure-sensitive hydrogels", Proceed. 24th Annual Meeting Adhession Soc., pp. 137-140, (2001).
Feldstein et al., "Contribution of molecular mobility to debonding of pressure-sensitive adhesive hydrogels", Polym. Mater. Sci. Eng., vol. 81, pp. 467-468, (1999).
Feldstein et al., "Effect of hydrophilic matrix hydration on transdermal drug delivery kinetics: I. The matrix hydration In Vivo and In Vitro", Prediction of Percutaneous Penetration, vol. 4b, pp. 61-64, Brian, et al., (Eds.) (1996).
Feldstein et al., "Effect of hydrophilic matrix hydration on transdermal drug delivery kinetics: II. In Vitro cytasine Delivery From Cypercuten TTS", Prediction of Percutaneous Penetration, vol. 4b, pp. 65-67, Brian, et al., (Eds.) (1996).
Feldstein et al., "Effect of hydrophilic matrix hydration on transdermal drug delivery kinetics: III. In Vitro clonide delivery from clopercuten TTS", Prediction of Percutaneous Penetration, vol. 4b, pp. 68-70, Brian, et al., (Eds.) (1996).
Feldstein et al., "Effect of hydrophilic matrix hydration on transdermal drug delivery kinetics: IV. In Vitro-In Vivo correlation," Prediction of Percutaneous Penetration, vol. 4b, pp. 71-73, Brian, et al., (eds.) (1996).
Feldstein et al., "Effects of chains orientation, free volume and interaction on glass transition in poly(N-vinyl pyrrolidone)-poly(ethylene glycol) blends involving a stoichiometric hydrogen-B bonded network complex", Polym. Mater. Sci. Eng., vol. 82, pp. 365-366, (2000).
Feldstein et al., "General approach to the molecular design of hydrophilic pressure-sensitive adhesives," Proc. 25th Ann. Mtg. and 2nd World Congress on Adhesion and Related Phenomena, Orlando, FL, vol. 1, pp. 292-294 (2002).
Feldstein et al., "Molecular insight into rheological and diffusion determinants of pressure sensitive adhesion", Proceed. 23rd Annual Meeting Adhesion Soc., pp. 54-56, (2000).
Feldstein et al., "Peculiarities of glass transition temperature relation to the composition of poly(N-vinyl pyrrolidone) blends with short chain poly(ethylene glycol)", Polymer, vol. 42, pp. 7719-7726, (2001).
Feldstein et al., "Quantitative relationship between molecular structure and adhesion of PVP-PEG hydrogels", Polym. Mater. Sci Eng., vol. 81, pp. 465-466, (1999).
Feldstein et al., "Relation of glass transition temperature to the hydrogen bonding degree and energy in poly(N-vinyl pyrrolidone) blends with hydroxyl-containing plasticizers: 2. Effects of poly(ethylene glycol) chain length", Polymer, vol. 42, pp. 981-990, (2001).
Feldstein et al., "Universal hydrophilic drug-containing adhesive matrix for systemic and topical transdermal drug delivery", Proc. 1st World Meeting APGI/APV, Budapest, 9/11, 2 pages, (1995).
Feldstein et al., "A new class of pressure-sensitive adhesives based on interpolymer and polymer-oligomer complexes", Polymer Science, vol. 51, No. 7, pp. 799-814 (2009).
Handbook of Pharmaceutical Excipients, Arther H. Kibbe, ed., 3rd ed., pp. 401-406, (2000).
Hawley's Condensed Chemical Dictionary, 14th Edition, Citation, "Oligomer, A polymer molecule of only a few monomer units (dimer, trimer, tetramer)", John Wiley and Sons, Inc., (2002).
International Search Report for PCT/US2000/18557 mailed Oct. 17, 2000.
International Search Report for PCT/US2001/21417 mailed Feb. 25, 2002.
International Search Report for PCT/US2002/13680 mailed Sep. 18, 2002.
International Search Report for PCT/US2002/14260 Mailed Sep. 17, 2002.
International Search Report for PCT/US2002/14725 mailed Sep. 27, 2002.
International Search Report for PCT/US2003/16408 Mailed Dec. 8, 2003.
International Search Report for PCT/US2003/039717 Mailed Jun. 28, 2004.
International Search Report for PCT/US2004/003443 Mailed Aug. 20, 2004.
International Search Report for PCT/US2004/011567 Mailed Jan. 10, 2006.
International Search Report for PCT/US2004/015448 Mailed Dec. 28, 2004.
International Search Report for PCT/US2004/029620 Mailed Jun. 1, 2005.
International Search Report for PCT/US2005/0002873 Mailed Apr. 27, 2005.
International Search Report for PCT/US2005/0034439 Mailed Jul. 19, 2006.
International Search Report for PCT/US2005/0046577 Mailed Jul. 26, 2006.
International Search Report for PCT/US/2005/028063 Mailed Apr. 28, 2006.
International Search Report for PCT/US/2005/032525 Mailed Mar. 17, 2006.
International Search Report for PCT/US/2006/000098 Mailed Nov. 3, 2006.
International Search Report for PCT/US2006/0003091 Mailed Oct. 11, 2006.
International Search Report for PCT/US2006/018500 Mailed Sep. 21, 2006.
Kotomin et al., "Squeeze-recoil analysis of adhesive hydrogels and elastomers", Polym. Mater. Sci. Eng., vol. 81, pp. 425-426, (1999).
Kotomin et al., "Durability and fracture of some visceolastic adhesives," Proceed. of the 23rd Annual Meeting of the Adhesion Soc., pp. 413-415, (Feb. 20-23, 2000).
MSDS (Material Safety Data Sheet), Lactic Acid, No. L0522, (2008).
Patent Abstracts of Japan, vol. 017, No. 055 (C-I023) Feb. 3, 1993 & JP 04 266818 A (Sekisui Chem Co Ltd), Sep. 22, 1992 abstract.
Roos et al., "Probe tack investigation of poly(vinyl pyrrolidone)-poly(ethylene glycol) blends", Proceed. 24th Annual Meeting Adhesion Soc., pp. 277-279, (2001).
Schehlmann "Polyvinylcaprolactam: physical and cosmetic properties of a new hair fixative resin", Lecture held at the In-Cosmetics, SOFW-Journal-Sounderdruck, Dusseldorf, 6 pages (1997).
Sintov et al., "Radiofrequency-driven skin microchanneling as a new way for electically assisted transdermal delivery of hydrophilic drugs", J. Contr.Release, vol. 89, pp. 311-320, (2003).
Supplementary European Search Report for EP04783729.9 Mailed Jun. 5, 2009.
Vartapian et al., "Self-diffusion in poly(N-vinyl pyrrolidone)-poly(ethylene glycol) systems", Colloid Polym. Sci., vol. 279, pp. 532-538, (2001).
Vartapian et al., "Molecular dynamics in poly(N-vinyl pyrrolidone)-poly(ethylene glycol) blends by pulsed-field gradient NMR method: effects of aging, hydration and PEG chain length", Macromol. Chem. Phys., vol. 202, pp. 2648-2652, (2001).
Whelan Polymer Technology Dictionary, Citation *Butyl Rubber*, Chapman Hall, 2-6 Boundry Row, London, UK, vol. 1, pp. 53 (1994).

\* cited by examiner

RAPIDLY DISSOLVING FILM FOR DELIVERY OF AN ACTIVE AGENT

CROSS-REFERENCE TO RELATED APPLICATIONS

This application is a continuation of U.S. patent application Ser. No. 11/047,964, filed Jan. 31, 2005, now U.S. Pat. No. 8,658,201, which claims priority under U.S.C. §119(e)(1) to Provisional U.S. Patent Application Ser. No. 60/540,852, filed Jan. 30, 2004. The disclosures of the aforementioned applications are incorporated by reference in their entireties.

TECHNICAL FIELD

This invention relates generally to rapidly dissolving films. More particularly, the invention relates to films useful as active agent delivery systems, in which an active agent is administered topically, transdermally, or transmucosally.

BACKGROUND

There are numerous systems that have been designed to deliver active agents to a moist environment such as the oral cavity. Such systems are particularly desirable in comparison to tablets, capsules and other dosage forms that must be swallowed, especially when the patient population includes children, the elderly, or other patients that may have difficulty swallowing.

As described in U.S. Pat. No. 6,750,921 to Kim et al., film-forming agents have been used to manufacture drug delivery formulations for percutaneous or transdermal application, but these necessarily involve an adhesive composition to retain the agent in situ long enough to effect sustained release of the active ingredient.

U.S. Pat. No. 6,264,891 to Zhang et al. describes systems that can be formulated as oral transmucosal patches, lozenges or troches, lollipops or chewing gum. However, these systems can have a relatively long life in the mouth, which may not always be desirable or practical.

Bioerodible films are described in Tapolsky et al., U.S. Pat. No. 5,800,832. The films have an adhesive layer and a non-adhesive backing layer and are intended to adhere to the mucosal surface. Biegajski et al., U.S. Pat. No. 5,700,478, describes a water-soluble pressure-sensitive mucoadhesive suitable for use in a mucosal-lined body cavity.

More recently, rapidly dissolving films have been developed. These include the instant wettability mucoadhesive film intended to adhere to the oral mucosa described in U.S. Pat. Nos. 5,948,430 and 6,709,671 to Zerbe et al. U.S. Pat. No. 6,596,298 to Leung et al. describes fast dissolving orally consumable films that are made of a film-forming polymer, preferably pullulan, to deliver antimicrobial agents and other active agents. These films are nontacky when dry but become tacky upon application to mucosal tissue. Mucoadhesion may not always be desired, however, because the difficulty of properly applying the film decreases patient compliance.

U.S. Patent Publication No. US 2002/0131990 A1, on the other hand, describes a pullulan-free edible film, and indicates that pullulan is costly and not readily available.

A method has recently been developed for tailoring the adhesive properties of polymer compositions useful in a number of applications, including pharmaceutical and cosmetic products. The method is based on new insights into the molecular mechanisms underlying adhesive properties. See, for example, Feldstein et al. (1999) *Polym. Mater. Sci. Eng.*, 81:465-466; Feldstein et al., *General approach to the molecular design of hydrophilic pressure-sensitive adhesives*, Proceed. 25th Annual Meeting Adhesion Soc. and 2nd World Congress on Adhesion and Relative Phenomena, February 2002, Orlando, Fla., vol.1 (Oral Presentations), p. 292-294; and Chalykh et al. (2002) *J. Adhesion* 78(8):667-694. As discussed in the foregoing references, pressure-sensitive adhesion results from the coupling of two apparently incompatible types of molecular structures, and there is a fine balance between strong cohesive interaction energy and enhanced "free volume."

That is, enhanced free volume in the molecular structure of a PSA (pressure-sensitive adhesive) polymer composition correlates with high tack exhibited at the macroscopic level and a liquid-like fluidity of the PSA material, which, in turn, allow for rapid formation of an adhesive bond. The "cohesive interaction energy" or "cohesion energy" defines the cohesive toughness of the PSA composition and provides the dissipation of detachment energy in the course of adhesive joint failure. Based on these findings, a general method for obtaining novel hydrophilic adhesives was developed and is described in U.S. Pat. No. 6,576,712 to Feldstein et al. In one embodiment, that method involves physically mixing a non-adhesive, hydrophilic, high molecular weight polymer with a relatively low molecular weight plasticizer capable of crosslinking the polymer via hydrogen bonding.

In spite of the development of the art, there remains a need for rapidly dissolving films that have significant drug loading capability, provide ease of handling, dissolve rapidly in the mouth or other moist body location, release drug instantly, and can provide sustained and controlled release of a variety of active agents.

BRIEF SUMMARY OF THE INVENTION

The invention addresses the aforementioned need in the art by providing a rapidly dissolving film that meets the desired criteria enumerated above. In one embodiment, then, the invention provides:

a film for administration of an active agent to a body surface, the film comprising:

(a) a film-forming binder comprising a hydrophilic polymer;

(b) a rapidly dissolving polymeric material; and (c) an effective amount of an active agent, wherein the film-forming binder and the rapidly dissolving material are effective to facilitate dissolution of the film within about 10 minutes following application of the film to a moist body surface.

The film is preferably nontacky during storage and prior to application, and thus may be readily removed from any packaging to be placed within the active agent delivery area, e.g., under the tongue. The ratio of components is generally selected so that the film is not mucoadhesive, i.e., the film cannot stick to mucosal surfaces. The rapid dissolving action may also serve to prevent adhesion to the body surface on which the film is placed.

The film dissolves rapidly in a moist environment and therefore facilities rapid release of the active agent following application of the film to a body surface. By "rapidly dissolving" is meant that the film typically dissolves in less than about 10 minutes following application, generally taking at least 5 seconds, preferably at least 30 seconds. Because of the close association of active agent with the film, in a preferred embodiment, the active agent is delivered rapidly as well.

DETAILED DESCRIPTION OF THE INVENTION

Before describing the present invention in detail, it is to be understood that unless otherwise indicated this invention is not limited to specific materials or manufacturing processes, as such may vary. It is also to be understood that the terminology used herein is for the purpose of describing particular embodiments only, and is not intended to be limiting. It must be noted that, as used in this specification and the appended claims, the singular forms "a," "an," and "the" include plural referents unless the context clearly dictates otherwise. Thus, for example, reference to "a hydrophilic polymer" includes not only a single hydrophilic polymer but also a combination or mixture of two or more different hydrophilic polymers, reference to "a rapidly dissolving material" includes a combination or mixture of two or more different rapidly dissolving materials as well as a single rapidly dissolving material, and the like.

In describing and claiming the present invention, the following terminology will be used in accordance with the definitions set out below.

The definitions of "hydrophobic" and "hydrophilic" polymers are based on the amount of water vapor absorbed by polymers at 100% relative humidity. According to this classification, hydrophobic polymers absorb only up to 1 wt % water at 100% relative humidity ("rh"), while moderately hydrophilic polymers absorb 1-10% wt % water, hydrophilic polymers are capable of absorbing more than 10 wt % of water, and hygroscopic polymers absorb more than 20 wt. % of water. A "water-swellable" polymer is one that absorbs an amount of water greater than at least 25 wt. % of its own weight, and preferably at least 50 wt. % of its own weight, upon immersion in an aqueous medium.

The term "noncovalent" bonding includes hydrogen bonding, electrostatic (ionic) bonding, or any other weak interaction such as Van Der Waals and hydrophobic interactions.

The term "polymer" or "polymeric material" includes linear and branched polymer structures, and also encompasses crosslinked polymers as well as copolymers (which may or may not be crosslinked), thus including block copolymers, alternating copolymers, random copolymers, and the like. Those compounds referred to herein as "oligomers" are polymers having a molecular weight below about 1000 Da, preferably below about 800 Da.

The terms "active agent," "pharmacologically active agent" and "drug" are used interchangeably herein to refer to a chemical material or compound that induces a desired pharmacological, physiological effect, and include agents that are therapeutically effective, prophylactically effective, or cosmeceutically effective. The terms also encompass pharmaceutically acceptable, pharmacologically active derivatives and analogs of those active agents specifically mentioned herein, including, but not limited to, salts, esters, amides, prodrugs, active metabolites, inclusion complexes, analogs, and the like. When the terms "active agent," "pharmacologically active agent" and "drug" are used, it is to be understood that both the active agent per se as well as pharmaceutically acceptable, pharmacologically active salts, esters, amides, prodrugs, active metabolites, inclusion complexes, analogs, etc., are included.

The term "effective amount" of an active agent is meant a nontoxic but sufficient amount of an active agent to provide the desired effect. The term "effective amount" or "a therapeutically effective amount" of a drug or pharmacologically active agent is intended to mean a nontoxic but sufficient amount of the drug or agent to provide the desired therapeutic effect. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation. Furthermore, the exact "effective" amount of an active agent incorporated into a composition of the invention is not critical, so long as the concentration is within a range sufficient to permit ready application of the formulation so as to deliver an amount of the active agent that is within a therapeutically effective range.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

The term "surface" as in "mucosal" surface or "body surface" is intended to include body surfaces such as skin, nails and mucosal tissue (e.g., sublingual, buccal, vaginal, rectal, urethral), as well as surfaces in and around the oral cavity (e.g., teeth, lips, gums, mucous membranes), as well as the surface of various skin wounds.

"Transmucosal" drug delivery is meant administration of a drug to the mucosal surface (e.g., sublingual, buccal, and other oral tissue; vaginal, rectal, ocular, gastrointestinal, and urethral tissue) of an individual so that the drug passes through the mucosal tissue and into the individual's blood stream, thereby providing a systemic effect. The term "transmucosal" is also intended to cover local effects, and therefore includes topical delivery of an agent to the mucosa, as in, for example, the treatment of various mucosal disorders to provide a local effect.

The terms "tack" and "tacky" are qualitative. However, the terms "substantially nontacky" "slightly tacky" and "tacky," as used herein, may be quantified using the values obtained in a PKI or TRBT tack determination method, as follows. By "substantially nontacky" is meant a composition that has a tack value that is less than about 25 g-cm/sec, by "slightly tacky" is meant a composition that has a tack value in the range of about 25 g-cm/sec to about 100 g-cm/sec, and by "tack" is meant a composition that has a tack value of at least 100 g-em/sec.

The term "plasticizer" is used in the conventional sense of the term to refer to a relatively low molecular weight compound that is miscible with a polymer or polymer blend and decreases the glass transition temperature and elastic modulus thereof.

The term "locally" refers to an effect within close proximity of the site of application, or more specifically within an area contiguous with the same tissue as the site of application. Compositions of the invention applied locally will remain within a distance of the site of application determined by the diffusion properties of the composition.

The term "systemically" refers to an effect within a region distal from the site of application up to and including the entire body as transported by the circulatory system.

The rapidly dissolving film composition of the invention is intended for use in any environment of the body that can provide sufficient moisture to dissolve the film and may find utility as pharmaceutical compositions for the treatment of various disorders, diseases, or other adverse physiological conditions. The film provides quick dissolution and action of active agents contained therein. Suitable moist body environments include, by way of illustration and not limitation those environments having mucosal tissue such as the oral cavity, the vagina, the urethra, the eye, the gastrointestinal tract, and the rectum. Skin or integument that is externally moisturized is also applicable. Since the film rapidly dissolves in an aqueous environment, drug delivery can be achieved by transmucosal delivery across a body surface. While local delivery is most typical, the invention also contemplates systemic delivery such as may occur with oral placement of the rapidly dissolving film after the film dissolves and drug is released, some of which may be swallowed.

The film comprises a film-forming binder, an effective amount of an active agent, and a rapidly dissolving polymeric material. The film-forming binder comprises a hydrophilic polymer, and may or may not be noncovalently bound to the active agent. The film-forming binder may also be a blend of a hydrophilic polymer and a complementary oligomer capable of hydrogen bonding to the hydrophilic polymer.

The film is preferably non-tacky during application and thus easily removed from packaging material and placed within a designated area, for example under the tongue. In one embodiment, the ratio of components is selected so that the film is not mucoadhesive, i.e., it does not stick to any mucosal surface. In addition, the rapidly dissolving action may also serve to prevent adhesion from taking place.

The film-forming binder and the rapidly dissolving material are effective in combination, as the film dissolves, to facilitate the release of active agent within about 10 minutes following application of the film to a moist body surface. The film dissolves rapidly in a moist environment and is useful for delivering a variety of active agents for indications where instant onset of pharmacological activity is desired. The term "rapidly" is intended to mean that the film dissolves in less than about 10 minutes after being applied, preferably within about 5 seconds to 10 minutes after application, optimally within about 30 seconds to 10 minutes after application. The film is designed to release the active agent within the time frame of the dissolution of the film. In one embodiment, the film begins to release drug within about 30 seconds to 10 minutes after being placed within a moist environment such as the oral cavity. In other embodiments, the film releases drug in less than about 30 seconds after administration.

The film forming binder is comprised of a hydrophilic polymer or a blend of a hydrophilic polymer and a plasticizer, e.g., a complementary oligomer capable of noncovalent bonding to the hydrophilic polymer and optionally capable of ionic or covalent bonding to the hydrophilic polymer as well. The hydrophilic polymer is generally a relatively high molecular weight polymer, and the plasticizer is generally an oligomer of substantially lower molecular weight. Although the complementary oligomer is not required, its inclusion may facilitate precise tailoring of the film properties. When a complementary oligomer is present, the weight ratio of the hydrophilic polymer to complementary oligomer will be in the range of about 10:1 to 1:10, preferably in the range of about 1.5:1 to about 3:1, and optimally is about 2:1.

Suitable hydrophilic polymers include repeating units derived from one or more monomers selected from an N-vinyl lactam monomer, a carboxy vinyl monomer, a vinyl ester monomer, an ester of a carboxy vinyl monomer, a vinyl amide monomer, and a hydroxy vinyl monomer. Such polymers include, by way of example, poly(N-vinyl lactams), poly(N-vinyl amides), poly(N-vinyl acrylamides), poly(N-alkylacrylamides), poly(N-vinyl acetamides), substituted and unsubstituted acrylic and methacrylic acid polymers (e.g., polyacrylic acids and polymethacrylic acids), polyvinyl alcohol (PVA), polyvinylamine, copolymers thereof and copolymers with other types of hydrophilic monomers (e.g. vinyl acetate), as well as combinations.

The poly(N-vinyl lactams) useful herein are preferably noncrosslinked homopolymers or copolymers of N-vinyl lactam monomer units, with N-vinyl lactam monomer units representing the majority of the total monomeric units of a poly (N-vinyl lactams) copolymer. Preferred poly(N-vinyl lactams) for use in conjunction with the invention are prepared by polymerization of one or more N-vinyl lactam monomers such as N-vinyl-2-pyrrolidone, N-vinyl-2-valerolactam, and N-vinyl-2-caprolactam. Non-limiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate. Poly (N-alkylacrylamides) include, by way of example, poly(methacrylamide) and poly (N-isopropyl acrylamide) (PNIPAM).

Polymers of carboxy vinyl monomers are typically formed from acrylic acid, methacrylic acid, crotonic acid, isocrotonic acid, itaconic acid and anhydride, a 1,2-dicarboxylic acid such as maleic acid or fumaric acid, maleic anhydride, or mixtures thereof, with preferred hydrophilic polymers within this class including polyacrylic acid and polymethacrylic acid, with polyacrylic acid most preferred.

Preferred hydrophilic polymers herein are the following: poly(N-vinyl lactams), particularly polyvinyl pyrrolidone (PVP) and polyvinyl caprolactam (PVCap); poly(N-vinyl acetamides), particularly polyacetamide per se; polymers of carboxy vinyl monomers, particularly polyacrylic acid and polymethacrylic acid; and copolymers and blends thereof. PVP and PVCap are particularly preferred.

The molecular weight of the hydrophilic polymer is not critical; however, the number average molecular weight of the hydrophilic polymer is generally in the range of approximately 100,000 to 2,000,000, more typically in the range of approximately 500,000 to 1,500,000.

The hydrophilic polymer may be combined with a compound effective to plasticize the polymer. Suitable plasticizers include, by way of illustration and not limitation: alkyl and aryl phosphates such as tributyl phosphate, trioctyl phosphate, tricresyl phosphate, and triphenyl phosphate; alkyl citrates and citrate esters such as trimethyl citrate, triethyl citrate and acetyl triethyl citrate, tributyl citrate and acetyl tributyl citrate, acetyl triethyl citrate, and trihexyl citrate; alkyl glycerolates; alkyl glycolates; dialkyl adipates such as dioctyl adipate (DOA; also referred to as bis(2-ethylhexyl) adipate), diethyl adipate, di(2-methylethyl)adipate, and dihexyl adipate; dialkyl phthalates, dicycloalkyl phthalates, diaryl phthalates and mixed alkyl-aryl phthalates, including phthalic acid esters, as represented by dimethyl phthalate, diethyl phthalate, dipropyl phthalate, dibutyl phthalate, di(2-ethylhexyl)-phthalate, di-isopropyl phthalate, diamyl phthalate and dicapryl phthalate; dialkyl sebacates such as diethyl sebacate, dipropyl sebacate, dibutyl sebacate and dinonyl sebacate; dialkyl succinates such as diethyl succinate and dibutyl succinate; dialkyl tartrates such as diethyl tartrate and dibutyl tartrate; glycol esters and glycerol esters such as glycerol diacetate, glycerol triacetate (triacetin), glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate; hydrophilic surfactants, preferably hydrophilic non-ionic surfactants such as, for example, partial fatty acid esters of sugars, polyethylene glycol fatty acid esters, polyethylene glycol fatty alcohol ethers, and polyethylene glycol sorbitan-fatty acid esters, as well as non-ionic surfactants such as ethylcellosolve; lower alcohols from ethyl to octyl; sorbitol; tartaric acid esters such as dibutyl tartrate; and mixtures thereof.

A preferred plasticizer for use in conjunction with the present invention is a bifunctional oligomer that is "complementary" to the film-forming binder as described in U.S. Pat. No. 6,576,712 to Feldstein et al., cited earlier herein. Preferably, the complementary oligomer is terminated with hydroxyl groups, amino or carboxyl groups. The oligomer typically has a glass transition temperature $T_g$ in the range of about −100° C. to about −30° C. and a melting temperature $T_m$ lower than about 20° C. The oligomer may be also amorphous. The difference between the $T_g$ value of the film-forming binder and that of the complementary oligomer is preferably greater than about 50° C., more preferably greater than about 100° C., and most preferably in the range of about 150° C. to about 300° C. Generally, the oligomer will have a molecular weight in the range from about 45 to about 800, preferably in the range of about 45 to about 600. Examples of suitable oligomers include, but are not limited to, low molecular weight polyalcohols (e.g. glycerol), oligoalkylene glycols such as ethylene glycol and propylene glycol, ether alcohols (e.g., glycol ethers), alkane diols from butane diol to octane diol, including carboxyl-terminated and amino-terminated derivatives of polyalkylene glycols. Polyalkylene glycols, optionally carboxyl-terminated, are preferred herein, and polyethylene glycol having a molecular weight in the range of about 300 to 600 is an optimal complementary oligomer.

The films of the invention may also include two or more plasticizers in combination, e.g., triethyl citrate and tributyl citrate, triethyl citrate and polyethylene glycol 400, polyethylene glycol 400 and dioctyl phthalate, etc.

The film further comprises at least one at least one rapidly dissolving polymeric material. Exemplary materials include water-soluble sugars, semi-synthetic and synthetic polymers, and commercially available disintegrants.

Suitable rapidly dissolving sugars are pharmaceutically acceptable monosaccharides, disaccharides, polysaccharides, and sugar alcohols. Exemplary monosaccharides include arabinose, erythrose, fructose, galactose, glucose and glucose monohydrate, D-mannose, ribose, ribulose, sorbose, threose, and xylose. Exemplary disaccharides include lactitol, lactose, maltitol, maltose, maltulose, sucrose, and trehalose. Exemplary polysaccharides include amylopectin, amylose, chitin, dextran, glucuronan, levan, mannan, maltodextrin, and pectin. Exemplary sugar alcohols include erythritol, hydrogenated isomaltulose, lactitol, maltitol, mannitol, sorbitol, and xylitol.

Maltodextrins are of particular interest, and are blends of saccharides, typically containing mono, di, tri and longer length polysaccharides (50% and higher of longer chain polysaccharides). The chain length of the polysaccharide affects both water solubility (i.e., longer chain molecules are less soluble) and film-forming capability (longer chain molecules form films more effectively). Thus, maltodextrins can be selected with polysaccharide ratios that optimize their utility as rapidly dissolving materials for use in the films of the invention.

Commercially available polymers suitable as rapidly dissolving materials herein include cellulose derivatives having molecular weights within the range of about 1,000 to 300,000. Exemplary cellulose derivatives include methylcellulose, carboxymethylcellulose, and hydroxypropylcellulose.

Other rapidly dissolving polymers include polyvinyl alcohol-polyethylene glycol graft copolymers such as those commercially available as Kollicoat-IR® from BASF AG (Germany) and Eudragit RD1000 from Rohm Pharma (Germany), as well as pH-sensitive fast dissolving polymers in the Eudragit® family of acrylate and methacrylate copolymers and terpolymers.

A single film of the invention can accommodate a drug loading of up to about 300 mg/cm$^2$ of active agent, but will typically contain about 100 μg/cm$^2$ to 200 mg/cm$^2$ of active agent. In a preferred embodiment, the film can accommodate a drug loading within the range of about 10 mg/cm$^2$ to 200 mg/cm$^2$. Optimally, the drug loading is within the range of about 1 mg/cm$^2$ to about 100 mg/cm$^2$.

In one embodiment, the active agent is readily soluble in the rapidly dissolving film. However, for less soluble drugs, a surfactant can be added to improve the drug's solubility characteristics. In other embodiments, such as for insoluble or high molecular weight agents, the agent can be contained in discrete particles, e.g., controlled release particles, dispersed throughout the film.

Suitable active agents that may be incorporated into the present films and delivered systemically (e.g., with a transdermal, oral, or other dosage form suitable for systemic administration of a drug) include, but are not limited to: analeptic agents; analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, antianginal agents, central nervous system (CNS) agents, beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids, including progestogens, estrogens, corticosteroids, androgens and anabolic agents; smoking cessation agents; sympathomimetics; tranquilizers; and vasodilators including general coronary, peripheral and cerebral. Specific active agents with which the present adhesive compositions are useful include, without limitation, anabasine, capsaicin, isosorbide dinitrate, aminostigmine, nitroglycerine, verapamil, propranolol, silabolin, foridone, clonidine, cytisine, phenazepam, nifedipine, fluacizin, and salbutamol.

For topical drug administration, suitable active agents include, by way of example, the following:

Bacteriostatic and bactericidal agents: Suitable bacteriostatic and bactericidal agents include, by way of example: halogen compounds such as iodine, iodopovidone complexes (i.e., complexes of PVP and iodine, also referred to as "povidine" and available under the tradename Betadine® from Purdue Frederick), iodide salts, chloramine, chlorhexidine, and sodium hypochlorite; silver and silver-containing compounds such as sulfadiazine, silver protein acetyltannate, silver nitrate, silver acetate, silver lactate, silver sulfate and silver chloride; organotin compounds such as tri-n-butyltin benzoate; zinc and zinc salts; oxidants, such as hydrogen peroxide and potassium permanganate; aryl mercury compounds, such as phenylmercury borate or merbromin; alkyl mercury compounds, such as thiomersal; phenols, such as thymol, o-phenyl phenol, 2-benzyl-4-chlorophenol, hexachlorophen and hexylresorcinol; and organic nitrogen compounds such as 8-hydroxyquinoline, chlorquinaldol, clioquinol, ethacridine, hexetidine, chlorhexedine, and ambazone.

Antibiotic agents: Suitable antibiotic agents include, but are not limited to, antibiotics of the lincomycin family (referring to a class of antibiotic agents originally recovered from *Streptomyces lincolnensis*), antibiotics of the tetracycline family (referring to a class of antibiotic agents originally recovered from *Streptomyces aureofaciens*), and sulfur-based antibiotics, i.e., sulfonamides. Exemplary antibiotics of the lincomycin family include lincomycin itself (6,8-dideoxy-6-[[(1-methyl-4-propyl-2-pyrrolidinyl)-carbonyl]amino]-1-thio-L-threo-α-D-galactooctopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]amino]-1-thio-L-threo-α-D-galacto-octopyranoside), related compounds as described, for example, in U.S. Pat. Nos. 3,475,407, 3,509,127, 3,544,551 and 3,513,155, and pharmacologically acceptable salts and esters thereof. Exemplary antibiotics of the tetracycline family include tetracycline itself, 4-(dimethylamino)-1,4,4α,5,5α,6,11,12α-octahydro-3,6,12,12α-pentahydroxy-6-methyl-1,1'-dioxo-2-naphthacenecarboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium.

Pain relieving agents: Suitable pain relieving agents are local anesthetics, including, but not limited to, acetamidoeugenol, alfadolone acetate, alfaxalone, amucaine, amolanone, amylocalne, benoxinate, betoxycaine, biphenamine, bupivacaine, burethamine, butacaine, butaben, butanilicaine, buthalital, butoxycaine, carticaine, 2-chloroprocaine, cinchocaine, cocaethylene, cocaine, cyclomethycaine, dibucaine, dimethisoquin, dimethocaine, diperadon, dyclonine, ecgonidine, ecgonine, ethyl aminobenzoate, ethyl chloride, etidocaine, etoxadrol, β-eucaine, euprocin, fenalcomine, fomocaine, hexobarbital, hexylcaine, hydroxydione, hydroxyprocaine, hydroxytetracaine, isobutyl p-aminobenzoate, kentamine, leucinocaine mesylate, levoxadrol, lidocaine, mepivacaine, meprylcaine, metabutoxycaine, methohexital, methyl chloride, midazolam, myrtecaine, naepaine, octacaine, orthocaine, oxethazaine, parethoxycaine, phenacaine, phencyclidine, phenol, piperocaine, piridocaine, polidocanol, pramoxine, prilocaine, procaine, propanidid, propanocaine, proparacaine, propipocaine, propofol, propoxycaine, pseudococaine, pyrrocaine, risocaine, salicyl alcohol, tetracaine, thialbarbital, thimylal, thiobutabarbital, thiopental, tolycaine, trimecaine, zolamine, and combinations thereof. Tetracaine, lidocaine and prilocaine are referred pain relieving agents herein.

Other topical agents that may be delivered using the films as drug delivery systems include the following: antifungal agents such as undecylenic acid, tolnaftate, miconazole, griseofulvine, ketoconazole, ciclopirox, clotrimazole and chloroxylenol; keratolytic agents, such as salicylic acid, lactic acid and urea; vessicants such as cantharidin; anti-acne agents such as organic peroxides (e.g., benzoyl peroxide), retinoids (e.g., retinoic acid, adapalene, and tazarotene), sulfonamides (e.g., sodium sulfacetamide), resorcinol, corticosteroids (e.g., triamcinolone), alpha-hydroxy acids (e.g., lactic acid and glycolic acid), alpha-keto acids (e.g., glyoxylic acid), and antibacterial agents specifically indicated for the treatment of acne, including azelaic acid, clindamycin, erythromycin, meclocycline, minocycline, nadifloxacin, cephalexin, doxycycline, and ofloxacin; skin-lightening and bleaching agents, such as hydroquinone, kojic acid, glycolic acid and other alpha-hydroxy acids, artocarpin, and certain organic peroxides; agents for treating warts, including salicylic acid, imiquimod, dinitrochlorobenzene, dibutyl squaric acid, podophyllin, podophyllotoxin, cantharidin, trichloroacetic acid, bleomycin, cidofovir, adefovir, and analogs thereof; and anti-inflammatory agents such as corticosteroids and nonsteroidal anti-inflammatory drugs (NSAIDs), where the NSAIDS include ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, and tiaprofenic acid.

For wound dressings, suitable active agents are those useful for the treatment of wounds, and include, but are not limited to bacteriostatic and bactericidal compounds, antibiotic agents, pain relieving agents, vasodilators, tissue-healing enhancing agents, amino acids, proteins, proteolytic enzymes, cytokines, and polypeptide growth factors.

The film can also include any pharmaceutically active agent useful in treating local physiological conditions involving the teeth and surrounding tissue, and mucosal tissues, as well as conditions that require systemic delivery of drugs. The active agent can be any substance that can be released from the composition to treat an undesirable physiological condition.

Amenable uses for transmucosal delivery across vaginal tissue include female contraception or administration of local antibiotics. Conditions involving rectal tissue treatment include hemorrhoids, while conditions that can be treated by transmucosal delivery across rectal tissue include pain management, and suppository antiemesis.

Other applications involving transmucosal drug delivery using the present films include treatment of conditions where immediate relief is needed. Such uses include treatment of anaphylactic shock with alpha adrenergics such as epinephrine; treatment of allergies with antihistaminic agents; treatment of a hypertensive event with antihypertensives; treatment of migraine headaches with sumatriptan, zomatriptan, 5HT blockers, and so forth; providing cough relief with antitussives and cough suppressants such as dextromethorphan; treatment of male erectile dysfunction with alpha adrenergics; treatment of nausea with anti-emetic agents; treatment of acute anxiety with beta blockers such as propranolol; providing local anesthesia with anesthetic agents; treating pain with analgesic agents such as fentanyl; and the treatment of addiction to agents such as nicotine, caffeine, and opiates.

Undesirable, physiological conditions involving the teeth or surrounding tissue which are amenable to oral care treatment with the present film include: halitosis; gingivitis; periodontal and oral infections; periodontal lesions; dental caries or decay; eradication of plaque-producing microbes; gingivitis; and other periodontal diseases, and can involve delivery of antibacterial and antimicrobial agents, breath fresheners, and so forth. In addition, the invention can also be useful in treating diseases of the esophagus and surrounding tissue, such as treating gastroenteritis and reflex esophagitis.

Suitable tooth-desensitizing agents that may be administered using the present films include potassium nitrate and strontium chloride. Suitable fluoride-containing anticavity agents include sodium fluoride, potassium fluoride and ammonium fluoride. Exemplary anti-tartar/anti-calculus agents that can be administered using the present films include phosphates such as pyrophosphates, polyphosphates, polyphosphonates (e.g., ethane-1-hydroxy-1,1-diphosphonate, 1-azacycloheptane-1,1-diphosphonate, and linear alkyl diphosphonates), and salts thereof; linear carboxylic acids; and sodium zinc citrate; and mixtures thereof. Preferred pyrophosphate salts are the di-alkali metal pyrophosphate salts; tetra-alkali metal pyrophosphate salts; and the hydrated or unhydrated forms of disodium dihydrogen pyrophosphate ($Na_2H_2P_2O_7$), tetrasodium pyrophosphate ($Na_4P_2O_7$), and tetrapotassium pyrophosphate ($K_4P_2O_7$). The pyrophosphate salts are described in more detail in Kirk & Othmer, Encyclopedia of Clinical Technology Third Edition, Volume 17, Wiley-Interscience Publishers (1982), the entire disclosure of which is herein incorporated by reference in its entirety. Tartar dissolving agents such as betaines, amine oxides and quaternaries, as described in U.S. Pat. No. 6,315,991 to Zofchak, may also be included.

Enzymatic agents that would act to inhibit the formation of plaque, calculus or dental caries can also be delivered using the present films. Suitable enzymes include, by way of example, proteases that break down salivary proteins which are absorbed onto the tooth surface and form the pellicle, or first layer of plaque; lipases which destroy bacteria by lysing proteins and lipids which form the structural component of bacterial cell walls and membranes; dextranases, glucanohydrolases, endoglycosidases, and mucinases which break down the bacterial skeletal structure which forms a matrix for bacterial adhesion to the tooth; and amylases which prevent the development of calculus by breaking-up the carbohydrate-protein complex that binds calcium. Preferred enzymes include any of the commercially available proteases, dextranases, glucanohydrolases, endoglycosidases, amylases, mutanases, lipases, mucinases, and compatible mixtures thereof.

Suitable nutritional supplements for local delivery to the teeth and surrounding tissue include vitamins (e.g., vitamins C and D, thiamine, riboflavin, calcium pantothenate, niacin, folic acid, nicotinamide, pyridoxine, cyanocobalamin, para-aminobenzoic acid, and bioflavonoids); and minerals (e.g., calcium, phosphorus, fluoride, zinc, manganese, and potassium); and mixtures thereof. Vitamins and minerals useful in the present invention are disclosed in Drug Facts and Comparisons (loose leaf drug information service), Wolters Kluer Company, St. Louis, Mo., 1997, pp 3-17; the entire disclosure of which is herein incorporated by reference.

The film can also include any cosmetically active agent to effect a desired change in the appearance of the teeth or surrounding tissue, or which imparts a socially desirable characteristic to the user, such as fresh breath. For example, a cosmetically active agent can be a breath freshener or an agent that whitens or bleaches the teeth. Exemplary tooth whitening agents include peroxides such as hydrogen peroxide, calcium peroxide, carbamide peroxide, as well as organic peroxides such as dialkyl peroxides such as t-butyl peroxide and 2,2bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide; metal chlorites such as calcium chlorite, barium chlorite, magnesium chlorite, lithium chlorite, sodium chlorite, and potassium chlorite; hypochlorite and chlorine dioxide; perborates; percarbonates; peroxyacids; and combinations thereof. Additional whitening agents may be included in the film. For example, surfactants such as detergents, may also be present, and will work together with the whitening agents described above to provide a brighter appearance to the teeth. In order to optimize whitening without demineralization of the teeth, calcium and/or fluoride salts can be included in the film.

For topical and transdermal administration of some active agents, and in wound dressings, it may be necessary or desirable to incorporate a permeation enhancer into the composition in order to enhance the rate of penetration of the agent into or through the skin. Suitable enhancers include, for example, the following: sulfoxides such as dimethylsulfoxide (DMSO) and decylmethylsulfoxide ($C_{10}MSo$); ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclaza-cycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. Mixtures of two or more enhancers may also be used.

Typically, the film composition, not including the active agent, can comprise about 0-50 wt % of the rapidly dissolving material, preferably about 0-40 wt %, and most preferably about 10-40 wt %; about 1-99 wt % of the hydrophilic polymer, preferably about 30-70 wt %, and more preferably about 40-60 wt %; and about 0-40 wt % of the complementary oligomer, preferably about 10-40 wt %, more preferably about 18-30 wt %. For those embodiments where the complementary oligomer is absent, the film composition, not including the active agent, can comprise about 0-50 wt % of the rapidly dissolving material, preferably about 0-40 wt %, and most preferably about 10-40 wt %; about 30-70 wt % of the hydrophilic polymer, preferably about 40-60 wt %.

The thickness of the resulting film, for most purposes, will be at least 1 mm. Typically, the thickness of the film is in the range of about 100 mm to about 200 mm, not including a release liner or other substrate that may be laminated to the film. By altering the concentration of various components, as will be appreciated by those of ordinary skill in the art, the film thickness, the film dissolution time, and the active agent release profile may be modified as desired.

The film can be cut into any desired configuration, e.g., circular, elliptical, square, rectangular, odd-shaped, and so forth. Generally the film will have a surface area within the range of about 1 cm² to about 6 cm², although larger and smaller sizes can be used to accommodate a particular utility or drug loading requirement.

The compositions of the invention are also generally melt extrudable, and thus may be prepared using a simple hot-melt blending and extruding process, with or without the addition of water. The components of the composition are weighed out and then admixed, for example using a Brabender or Baker Perkins Blender, generally although not necessarily at an elevated temperature, e.g., bout 100-170° C., and more typically 90-140° C. Solvents or water may be added if desired. The resulting composition can be extruded using a single or twin extruder, or pelletized. Alternatively, the components of the composition can be melted one at a time, and then mixed prior to extrusion.

Preferably the films of the invention are non-tacky and are not mucoadhesive. The preferred method of preparing such substantially nontacky compositions is solution casting. Solution casting involves admixing the components of the film composition (the rapidly dissolving material, film forming binder, active agent, and any other components to be included) in a suitable solvent. An aqueous solvent is used when the components are water soluble. However, other volatile solvents such as ethyl acetate, or lower alkanols (e.g., ethanol, isopropyl alcohol, etc.), or a lower alkanol/water mixture can also be used, typically at a concentration typically in the range of about 35% w/v to about 60% w/v. Such solvents are particularly useful when manufacturing with water-insoluble materials (viz. those materials having an aqueous solubility of less than 5 wt. % at 20° C. After preparation of the solution, the admixture is cast onto a substrate such as a release liner, as above. Both admixture and casting are preferably carried out at ambient temperature. The substrate coated with the film is then heated to remove the solvents. Evaporation occurs at temperatures within the range of about 70° C. to about 120° C. for aqueous solvents and about 50° C. to about 100° C. for non-aqueous solvents, for a time period in the range of about one to four hours, optimally about two hours.

In one embodiment, materials such as citric acid and sodium bicarbonate are included in the composition, the combination of which provides an effervescent effect in the casting solution, so that, when dried, the film becomes bubbly and porous.

The rate at which the film dissolves to release the active agent is a function of several factors including the microenvironment of the body surface on which the film is applied, the thickness of the film, the composition of the film, temperature and size and chemical nature of the active agent and additives. In the present invention the film typically dissolves within ten minutes of application to the moist body surface. Preferably the rate of dissolution is in the range of 30 seconds to 10 minutes.

The films of the invention may also include one or more conventional additives, which may be combined with the other components of the film during formulation or incorporated thereafter. Optional additives include, without limitation, fillers, pH regulating agents, tackifiers, detackifying agents, disintegrants, antimicrobial agents, antioxidants, preservatives, colorants, flavors, and combinations thereof.

Absorbent fillers may be advantageously incorporated to control the degree of hydration when the film is on the skin or other body surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, woven and non-woven paper and cotton materials. Other suitable fillers are inert, i.e., substantially non-adsorbent, and include, for example, polyethylenes, polypropylenes, polyurethane polyether amide copolymers, polyesters and polyester copolymers, nylon and rayon. A preferred filler is colloidal silica, e.g., Cab-O—Sil® (Cabot Corporation, Boston Mass.).

Compounds useful as pH regulators include, but are not limited to, glycerol buffers, citrate buffers, borate buffers, phosphate buffers, and citric acid-phosphate buffers. Buffer systems are useful to ensure, for instance, that the pH of a film of the invention, upon absorption of moisture, is compatible with that of an individual's body surface.

Tackifiers can also be included to render the film adhesive, should a particular application require the film to adhere to a body surface. Exemplary tackifying materials include tacky rubbers such as polyisobutylene, polybutadiene, butyl rubber, polystyrene-isoprene copolymers, polystyrene-butadiene copolymers, and neoprene (polychloroprene). Other examples of suitable tackifiers herein are those that are conventionally used with pressure sensitive adhesives, e.g., rosins, rosin esters, polyterpenes, and hydrogenated aromatic resins. In those embodiments wherein adhesion is to be reduced or eliminated, conventional detackifying agents may also be used. Suitable detackifiers include crosslinked poly (vinylpyrrolidone), silica gel, bentonites, and so forth.

Preferred thickeners herein are naturally occurring compounds or derivatives thereof, and include, by way of example: collagen; galactomannans; starches; starch derivatives and hydrolysates; cellulose derivatives such as methylcellulose, hydroxypropylcellulose, hydroxyethyl cellulose, and hydroxypropyl methylcellulose; colloidal silicic acids; and sugars such as lactose, saccharose, fructose and glucose. Synthetic thickeners such as polyvinyl alcohol, vinylpyrrolidone-vinylacetate-copolymers, polyethylene glycols, and polypropylene glycols may also be used.

Antimicrobial agents may also be added. Antimicrobial agents function by destroying microbes, preventing their pathogenic action, and/or inhibiting their growth. Desirable properties of antimicrobial agents include, but are not limited to: (1) the ability to inactivate bacteria, viruses and fungi, (2) the ability to be effective within minutes of application and long after initial application, (3) cost, (4) compatibility with other components of composition, (5) stability at ambient temperature, and (6) lack of toxicity. Antioxidants may be incorporated into the compositions of the invention in lieu of or in addition to any antimicrobial agent(s). Antioxidants are agents that inhibit oxidation and thus prevent the deterioration of preparations by oxidation. Suitable antioxidants include, by way of example and without limitation, ascorbic acid, ascorbyl palmitate, butylated hydroxyanisole, butylated hydroxytoluene, hypophosphorous acid, monothioglycerol, sodium ascorbate, sodium formaldehyde sulfoxylate and sodium metabisulfite and others known to those of ordinary skill in the art. Other suitable antioxidants include, for example, vitamin C, butylated hydroxytoluene (BHT), butylated hydroxyanisole (BHA), sodium bisulfite, vitamin E and its derivatives, propyl gallate, sulfite derivatives, and others known to those of ordinary skill in the art.

Other preservatives that can be incorporated into the present films include, by way of example, p-chloro-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

In practice, the films can be used simply by removing the product from its package, removing a release liner (when included) and placing the film in a moist environment, e.g., on or under the tongue, until it is erodes. The films described herein can be provided in a variety of sizes, depending upon their intended use, the amount of drug loading desired, the duration of erosion, the duration of drug delivery, and so forth. If desired, a translucent film can be provided, and is positioned without being obtrusive or noticeable to others.

The practice of the present invention will employ, unless otherwise indicated, conventional techniques of polymer chemistry, adhesive formulation, and drug delivery, which are within the skill of the art. Such techniques are fully explained in the literature.

It is to be understood that while the invention has been described in conjunction with the preferred specific embodiments thereof, the foregoing description, as well as the example that follows, is intended to illustrate and not limit the scope of the invention. Other aspects, advantages and modifications will be apparent to those skilled in the art to which the invention pertains.

All patents, patent applications, journal articles and other references cited herein are incorporated by reference in their entireties.

The following abbreviations and tradenames is used in the example:

HPC hydroxypropyl cellulose; MW 95,000
PEG 400 polyethylene glycol 400
PEG 540 polyethylene glycol 540
PG propylene glycol
PVP K90 Kollidon® 90F polyvinylpyrrolidone (BASF)
PVP VA 64 Kollidon® VA 64 polyvinylpyrrolidone (BASF)

EXAMPLE

Preparation of Rapidly Dissolving Films

Film compositions containing the components set forth in Table 1 were prepared by solution casting:

TABLE 1

| SAMPLE | RAPIDLY DISSOLVING MATERIAL | FILM FORMING BINDER | OTHER COMPONENTS |
|---|---|---|---|
| 1 | 10 wt % maltodextrin | 60 wt % PVP K90 30 wt % PEG 540 | none |
| 2 | 10 wt % maltodextrin | 60 wt % PVP K90 30 wt % PEG 540 | none |
| 3 | 10 wt % maltodextrin | 60 wt % PVP K90 30 wt % PEG 540 | none |
| 4 | 40 wt % HPC | 40 wt % PVP VA 64 18 wt % PG | 1.2 wt % citric acid; 0.8 wt % sodium bicarbonate |
| 5 | 40 wt % HPC | 40 wt % PVP VA 64 20 wt % PEG 400 | none |

Various characteristics of the films were evaluated, and the results are set forth in Table 2. "Disintegration time" in the mouth refers to the length of time seen for the film to lose its physical integrity. The "dissolution time" refers to the length of time for complete dissolution.

TABLE 2

| | Sample: | | | | |
|---|---|---|---|---|---|
| | 1 | 2 | 3 | 4 | 5 |
| Drug loading capacity (per cm$^2$): | up to 2 mg | up to 5 mg | up to 7 mg | up to 12 mg | up to 15 mg |
| Thickness (mil): | 1 | 3 | 15 | 8 | 12 |
| Disintegration time in the mouth: | <5 sec | 15-20 sec | 30-45 sec | 30-45 sec | 30-45 sec |
| Dissolution time in the mouth: | 10-15 sec | 60-90 sec | 1-2 min | 2-3 min | 3-4 min |
| Appearance and physical properties: | opaque, stiff, elastic | opaque, stiff, elastic | opaque, porous, bubbly, | opaque, stiff, elastic | clear, elastic |

We claim:

1. A film for administration of an active agent to a body surface, the film comprising:
    a blend comprised of a hydrophilic polymer and a plasticizer miscible with the hydrophilic polymer, the hydrophilic polymer and the plasticizer blended to form non-covalent bonds between the hydrophilic polymer and the plasticizer, wherein the hydrophilic polymer has an average molecular weight of approximately 100,000 to 2,000,000 Daltons and wherein the plasticizer is present in the film at a weight percent (wt%) of 10 to 40 wherein the wt% of the plasticizer is based on the film composition exclusive of the active agent,
    a rapidly dissolving polymeric material; and
    an effective amount of an active agent,
    wherein the blend and the rapidly dissolving material are effective to facilitate dissolution of the film within 10 minutes following application of the film to a moist body surface.

2. The film of claim 1, wherein the hydrophilic polymer comprises repeating units derived from monomers selected from N-vinyl lactam monomers, carboxy vinyl monomers, vinyl ester monomers, esters of a carboxy vinyl monomer, vinyl amide monomers, hydroxy vinyl monomers, and combinations thereof.

3. The film of claim 1, wherein the hydrophilic polymer is selected from poly(N-vinyl lactams), poly(N-vinyl amides), poly(N-vinyl acrylamides), poly(N-alkylacrylamides), poly(N-vinyl acetamides), substituted and unsubstituted acrylic and methacrylic acid polymers, polyvinyl alcohol, polyvinylamine, and copolymers and blends thereof.

4. The film of claim 1, wherein the hydrophilic polymer is selected from poly(N-vinyl lactams), poly(N-vinyl amides), poly(N-alkylacrylamides), and copolymers and blends thereof.

5. The film of claim 1, wherein the hydrophilic polymer is a poly(N-vinyl lactam).

6. The film of claim 1, wherein the hydrophilic polymer is a poly(N-vinyl lactam) homopolymer.

7. The film of claim 6, wherein the poly(N-vinyl lactam) is selected from polyvinyl pyrrolidone, polyvinyl caprolactam, and blends thereof.

8. The film of claim 7, wherein the poly(N-vinyl lactam) is polyvinyl pyrrolidone.

9. The film of claim 7, wherein the poly(N-vinyl lactam) is polyvinyl caprolactam.

10. The film of claim 1, wherein the hydrophilic polymer has a number average molecular weight in the range of approximately 500,000 to 1,500,000.

11. The film of claim 1, wherein the plasticizer is selected from the group consisting of dialkyl phthalates, dicycloalkyl phthalates, diaryl phthalates, mixed alkyl-aryl phthalates, alkyl phosphates, aryl phosphates, alkyl citrates, citrate esters, alkyl adipates, dialkyl tartrates, dialkyl sebacates, dialkyl succinates, alkyl glycolates, alkyl glycerolates, glycol esters, glycerol esters, and mixtures thereof.

12. The film of claim 1, wherein the plasticizer is selected from dimethyl phthalate, diethyl phthalate, dipropyl phthalate, di(2-ethylhexyl)phthalate, di-isopropyl phthalate, diamyl phthalate, dicapryl phthalate, tributyl phosphate, trioctyl phosphate, tricresyl phosphate, triphenyl phosphate, trimethyl citrate, triethyl citrate, tributyl citrate, acetyl triethyl citrate, trihexyl citrate, dioctyl adipate, diethyl adipate, di(2-methylethyl)adipate, dihexyladipate, diethyl tartrate, dibutyl tartrate, diethyl sebacate, dipropyl sebacate, dinonyl sebacate, diethyl succinate, dibutyl succinate, glycerol diacetate, glycerol triacetate, glycerol mono lactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate, triethylene glycol dipropionate, and mixtures thereof.

13. The film of claim 1, wherein the plasticizer is selected from tributyl phosphate, trioctyl phosphate, triphenyl phosphate, trimethyl citrate, triethyl citrate, and tributyl citrate.

14. The film of claim 1, comprising 40 to 60 wt% of the hydrophilic polymer, wherein the wt% of the hydrophilic polymer is based on the film composition exclusive of the active agent.

15. The film of claim 1, wherein the plasticizer is a bifunctional, linear oligomer having a functional group at each terminus, each of said terminal functional groups capable of non-covalently binding to the hydrophilic polymer.

16. The film of claim 15, wherein the bifunctional, linear oligomer has a molecular weight in the range of approximately 45 Daltons to approximately 800 Daltons.

17. The film of claim 15, wherein the bifunctional, linear oligomer is polyethylene glycol.

18. The film of claim 17, wherein the polyethylene glycol has a molecular weight of 400.

19. The film of claim 15, wherein the bifunctional, linear oligomer has a molecular weight in the range of approximately 45 Daltons to approximately 600 Daltons.

20. The film of claim 15, wherein the terminal functional groups are selected from hydroxyl, carboxy, and amino groups.

21. The film of claim 15, wherein the terminal functional groups are selected from hydroxyl and carboxy groups.

22. The film of claim 15, wherein the terminal functional groups are hydroxyl groups.

23. The film of claim 22, wherein the hydrophilic polymer and the plasticizer have a weight ratio of about 1:10 to 10:1.

24. The film of claim 22, wherein the hydrophilic polymer and the plasticizer have a weight ratio of about 1.5:1 to about 3:1.

25. The film of claim 22, wherein the hydrophilic polymer and the plasticizer have a weight ratio of about 2:1.

26. The film of claim 1, wherein the rapidly dissolving polymeric material is selected from the group consisting of oligosaccharides, polysaccharides, crosslinked polyvinylpyrrolidone, alginic acid, agar, and bentonite.

27. The film of claim 1, wherein the rapidly dissolving polymeric material is selected from oligosaccharides and polysaccharides.

28. The film of claim 1, wherein the rapidly dissolving polymeric material is a cellulose derivative having a molecular weight of between about 1,000 Daltons to 300,000 Daltons.

29. The film of claim 1, wherein the rapidly dissolving polymeric material is maltodextrin.

30. The film of claim 1, wherein the active agent is a pharmacologically active agent and the effective amount is a therapeutically effective amount.

31. The film of claim 30, wherein the active agent is a locally acting agent.

32. The film of claim 30, wherein the active agent is a systemically acting agent.

33. The film of claim 1, wherein the active agent is contained in discrete particles dispersed throughout the film.

34. The film of claim 1, which dissolves within about 5 to 30 seconds following application of the film to a moist body surface.

35. The film of claim 1, which dissolves in less than about 30 seconds following application of the film to a moist body surface.

36. The film of claim 1, having a thickness of at least one 1 mm.

37. The film of claim 1, having a thickness in the range of about 100 mm to 200 mm.

38. A method for administering an active agent to a patient, comprising placing the film of claim 1 on a moist body surface of the patient and allowing the film to dissolve.

39. The method of claim 38, wherein the moist body surface of the patient is mucosal tissue.

40. The method of claim 38, wherein the moist body surface is selected from skin that is externally moistened.

41. A film for administration of an active agent to a body surface, the film comprising:
(a) a blend consisting of (i) a hydrophilic polymer having an average molecular weight of approximately 100,000 to 2,000,000 Daltons, and (ii) about 10 to 40 wt% of a plasticizer having a molecular weight of between 45 to 800 Daltons, and (b) rapidly dissolving polymeric material, the hydrophilic polymer and the plasticizer blended to form non-covalent bonds between the hydrophilic polymer and the plasticizer, wherein the wt% of the plasticizer and of the rapidly dissolving polymeric material is each based on the film composition exclusive of the active agent; and an effective amount of an active agent, wherein the blend and the rapidly dissolving material are effective to facilitate dissolution of the film within 10 minutes following application of the film to a moist body surface.

42. The film of claim 41, wherein the hydrophilic polymer is selected from poly(N-vinyl lactams), poly(N-vinyl amides), poly(N-alkylacrylamides), and copolymers and blends thereof.

43. The film of claim 41, wherein the hydrophilic polymer is a poly(N-vinyl lactam).

44. The film of claim 43, wherein the poly(N-vinyl lactam) is polyvinyl pyrrolidone.

45. The film of claim 41, wherein the hydrophilic polymer has a number average molecular weight in the range of approximately 500,000 to 1,500,000 Daltons.

46. The film of claim 41, wherein the rapidly dissolving polymeric material is selected from the group consisting of oligosaccharides, polysaccharides, crosslinked polyvinylpyrrolidone, alginic acid, agar, and bentonite.

47. The film of claim 41, wherein the active agent is for treatment of a condition involving teeth or surrounding tissue.

* * * * *